United States Patent [19]

Morhenn

[11] Patent Number: 4,886,745
[45] Date of Patent: Dec. 12, 1989

[54] MONOCLONAL ANTIBODY SPECIFIC FOR HUMAN BASAL CELL SURFACE ANTIGEN

[75] Inventor: Vera Morhenn, Palo Alto, Calif.

[73] Assignee: Syntex Inc., Palo Alto, Calif.

[21] Appl. No.: 595,075

[22] Filed: Mar. 30, 1984

[51] Int. Cl.$^4$ .......................................... G01N 33/577
[52] U.S. Cl. ............................................ 435/7; 424/3;
424/7.1; 435/70.21; 435/172.2; 435/240.27;
435/948; 436/548; 436/800; 436/808; 436/813;
128/630; 128/751; 530/387; 530/388; 530/808;
530/809
[58] Field of Search .................. 935/106, 107, 108, 95,
935/110; 436/548, 800, 536, 808, 501, 503, 813;
435/68, 172.2, 240, 241, 948, 43, 7, 240.27;
260/112 R; 424/85, 86, 87, 3, 7.1; 128/630, 1,
1.1, 751

[56] References Cited

U.S. PATENT DOCUMENTS

| 4,361,544 | 11/1982 | Goldenberg | 424/1 |
| 4,443,427 | 4/1984 | Reinherz et al. | 424/1.1 |
| 4,448,890 | 5/1984 | Smetana et al. | 436/508 |

FOREIGN PATENT DOCUMENTS

WO-A-
8304313  8/1983  World Int. Prop. O.

OTHER PUBLICATIONS

Oseroff et al., Journal of Investigative Dermatology, vol. 84:257–261, 1985.
Oseroff et al., Clinical Research, vol. 30, No. 2:1982.
Morhenn et al., Journal of Investigative Dermatology, vol. 81:1275–/3/5, 1983.
Suter et al., Journal Immunologica Methods, vol. 39, 407–411, 1980.
Tromovich et al., Arch Dermatol, vol. 110: 231–232, Aug. 1974.
Frederic E. Mohs, Archives of Surgery, vol. 42:379–295, 1974.

*Primary Examiner*—Christine M. Nucker
*Attorney, Agent, or Firm*—Theodore J. Leitereg

[57] ABSTRACT

The present invention is concerned with novel monoclonal antibodies specific for an antigenic site on a protein characteristic of a human basal cell and a malignant squamous cell. The antibodies do not bind to mesenchymal cells such as fibroblasts and endothelial cells. The protein on the cell surface which binds to one of the antibodies has a molecular weight of about 120,000 as determined by one dimensional gel electrophoresis. The antibodies find use in diagnostic methods such as the detection of malignant cells, e.g., the detection of residual tumor cells in skin subjected to microscopically-controlled surgery.

10 Claims, No Drawings

MONOCLONAL ANTIBODY SPECIFIC FOR HUMAN BASAL CELL SURFACE ANTIGEN

The invention described herein was made in the course of work under a grant or award from the National Institutes of Health. The government has certain rights in this invention.

BACKGROUND OF THE INVENTION

1. Field of the Invention

Mohs' chemosurgery or microscopically-controlled surgery (MCS) described in *Arch. Surg.* 42:279–295 (1941) and the fresh tissue modification described by Tromovitch, et al. in *Arch. Dermatol.* 110:231–232 (1974) are used extensively to treat squamous cell carcinomas and certain types of basal cell carcinomas of the skin. These carcinomas are characterized by strands and nests of tumor cells which are not visible on the skin surface. Conventional forms of surgery and radiation often fail to eradicate these silent extensions of tumor so that relatively high recurrence rates result. In MCS, the clinically visible tumor is removed and the next layer of tissue is excised, immediately frozen, cut on a cryostat, stained with hematoxylin and eosin, and checked for residual tumor cells with a light microscope.

MCS is the treatment of choice in squamous cell carcinomas and recurrent basal cell carcinomas. With this form of therapy the cure rate for recurrent basal cell carcinomas is about 90% whereas the cure rate with other forms of therapy (e.g., radiation, conventional surgical excision) ranges from 50% to 85%. For squamous cell carcinomas MCS results in a 5-year cure rate of 94% in a group of patients who have not received previous treatment. However, in recurrent squamous cell carcinomas the 5-year cure rate is only 76.3%. Unsuccessful treatment of basal cell carcinomas causes increased morbidity, repeated treatments with the possibility of multilation, and economic losses. Recurrences of squamous cell carcinomas may lead to metastasis, which in Homs' series of squamous cell carcinomas led to death in 97 patients (4.3%).

Residual and undetected tumor cells are thought to be the main reason for recurrence after MCS. When single cells or small islands of tumor cells remain in the tissue, they are sometimes difficult to distinguish on frozen section with conventional staining methods since they may be confused with inflammatory, nerve, or vascular cells. Thus, a staining technique which clearly defines tumor cells should decrease the rate of recurrence and mortality. Furthermore, a definitive staining technique should lower the need for extensive experience in reading frozen sections and for taking extra tissue at the margins if the presence or absence of tumor cells is in doubt on the frozen sections of already removed skin.

2. Description of the Prior Art

A microscopically-controlled method of cancer excision is described in *Arch. Surg.* 42:279–295, 1941. A fresh tissue technique in microscopically-controlled excision of skin tumors is disclosed by Tromovitch, et al., in *Arch. Dermatol.* 110:231–232, 1974. Continuous cultures of fused cells secreting antibody of predefined specificity is described in Kohler, et al., *Nature* 265:495–497, 1975. A monoconal antibody against human basal cells which affects the growth of epidermal cells in vitro is disclosed by Oseroff, et al., in *Clin. Res.* 30:601A, 1982. A biotin-avidin-horseradish peroxidase method of detection of T and B cell antigens with hybridoma antibodies is described by Warnke, et al., in *J. Hostochem. Cytochem.* 28:771–776, 1980.

SUMMARY OF THE INVENTION

The present invention is concerned with novel monoclonal antibodies specific for an antigenic site on a protein characteristic of human basal cells, both normal and malignant. This antigenic site on the protein is also found on malignant squamous cells and, thus, the antibodies of the invention will also bind to malignant squamous cells. Preferably, these monoclonal antibodies are of the IgG type and bind specifically to a protein having a molecular weight of about 120,000 as determined by one dimensional gel electrophoresis. Preferably, these monoclonal antibodies bind to, but do not inhibit the growth of, normal basal cells. The monoclonal antibodies are secreted by a murine hybridoma.

The invention also concerns certain diagnostic methods employing the monoclonal antibodies of the invention. One such method involves the determination of the presence of tumor cells in a specimen suspected of containing such cells. The specimen is contacted with the monoclonal antibody, which is capable of distinguishing human basal cells and such tumor cells from other cell types which may be present in the specimen. The contact is carried out under conditions for binding of the antibody to the tumor cells. After contact, the presence or absence of binding of the antibody to the cells in the specimen is determined. This binding is related to the presence or absence of tumor cells in the specimen. An example of such a method is the detection of residual tumor cells, e.g., malignant squamous cells, in skin subjected to microscopically-controlled surgery to remove a tumor. Generally, the specimen is contacted with a labeled specific binding partner for the monoclonal antibody. This label is capable of producing a detectable signal.

DESCRIPTION OF THE SPECIFIC EMBODIMENTS

The present invention concerns certain diagnostic methods employing antibodies specific for an antigenic site characteristic of a normal human basal cell. One such method involves the determination of the presence of a malignant condition in mammalian tissue, for example, epithelial tissue and tissue composed in part of epithelial cells; e.g., the determination of the presence of malignant squamous cells in a specimen of such tissue suspected of containing such cells. The term "malignant condition" refers to the presence of displastic including carcinoma in situ, neoplastic, malignant; or tumor cells, or the like. The specimen is contacted or combined with a monoclonal antibody capable of distinguising human basal cells and malignant squamous cells from other cell types which may be present in the specimen. Usually, normal basal cells are not found in the specimen. The contact is carried out under conditions for binding of the antibody to the malignant squamous cells. After contact, the presence of binding of the antibody to the malignant cells in the specimen is observed. That is, the specimen is examined for immune complexes of the antibody and the antigenic site. This immune complex formation is related to the presence of malignant squamous cells in the specimen if normal basal cells are not present in the issue. When antibody binding cells are found in the specimen, the location of the binding cells may also be related to the presence of a malignant condition since the finding of basal cells outside, i.e., below, the basal layer is indicative of a malignant condition.

Monoclonal antibodies useful in the method of the invention may be produced according to the standard techniques of Kohler and Milstein, *Nature* 265:495–497, 1975. For example, epidermal cells from psoriatic plaques are used as the immunogen. The split thickness skin containing epidermal cells from psoriatic plaques is trypsinized and dispersed cells are obtained. These cells are injected into a mouse and, after a sufficient time, the mouse is sacrificed and spleen cells obtained. The spleen cell chromosomes encoding the base sequences for the desired immunoglobulins are immortalized by fusing the spleen cells with myeloma cells or with lymphoma cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies, so as to free the monoclonal antibodies from other proteins and other contaminants (see Kohler and Milstein, supra).

One such monoclonal antibody useful in the method of the present invention is exemplified by a novel antibody designated VM-2. This monoclonal antibody is a specific for an antigenic site on a protein characteristic of human basal cells, both normal and malignant. The antigenic site is also found on malignant squamous cells. The protein has little, if any, associated lipid. When lysates of biosynthetically labeled target cells are immunoprecipitated with VM-2 antibody and the precitates are submitted to sodium dodecyl sulfate-polyacrylamide one-dimensional gel electrophoresis (SDS-PAGE), the protein appears as a doublet (two bands) of molecular weight of about 120,000 daltons. The antibody is of the $IgG_1$ isotype. The VM-2 antibody does not bind to mesenchymal cells, such as fibroblasts or endothelial cells, nor to Staphylococcal Protein A at pH 7.3. The VM-2 antibody is produced by the VM-2 murine hybridoma.

Also included within the scope of the invention are useful binding fragments of the VM-2 monoclonal antibody such as Fab, F(ab')$_2$, Fv, and so forth. The antibody fragments are obtained by conventional techniques. For example, useful binding fragments may be prepared by peptidase digestion of the antibody using papain or pepsin.

While the above specific example of the novel antibodies of the invention is directed to an antibody of the IgG class from a murine source, this is not meant to be a limitation. The above antibody and those antibodies having functional equivalency with the above antibody, whether from a murine source, mammalian source including human, or other sources, or combinations thereof are included within the scope of this invention, as well as other classes such as IgM, IgA, IgE, and the like, including isotypes within such classes. By the term "functional equivalency" is meant that the antibody is capable of binding to the above-described antigenic site and capable of competing with the VM-2 antibody for such site. That is, such antibody, when combined with a specimen containing a cell or cell fragment having such antigenic site, will bind to such antigenic site and will block VM-2 antibody from binding to such site.

Another monoclonal antibody which may be used in the method of the present invention is disclosed in *Clin. Res.*, supra. The disclosed antibody was prepared using epidermal cells obtained from a psoriatic plaque. An antibody secreting hybridoma cell line was produced according to standard techniques. The monoclonal antibody which was produced was termed VM-1. The antibody is an $IgG_1$.

One difference between the VM-1 and the VM-2 antibodies is that the former inhibits the growth or basal cells whereas the latter does not inhibit such growth. Another difference is that the VM-1 monoclonal antibody does not bind to the same human basal cell surface antigen as the VM-2 monoclonal antibody. The antigen to which VM-1 binds is extractable with methanol and chloroform and is probably lipid in nature.

A particular example, by way of illustration and not limitation, of a method in accordance with the invention is a method for the detection of residual tumor cells in microscopically-controlled surgery of the skin. The dermis or deeper layers of the skin, where normal basal cells are usually not found, are examined for tumor cells. The above method is applied to a specimen which is a section of skin obtained after removal of the tumor. The section of skin obtained is adjacent to the tumor and generally is the next layer of tissue which is excised after excision of the tumor or after excision of a previous layer of skin. The layer of skin which is excised is treated to obtain sections of such skin, which treatment initially involves freezing the layer of skin or tissue, normally freezing immediately after excision. The frozen layer of tissue is then cut into sections using, for example, a cryostat.

The section of skin obtained as described above is contacted with a first monoclonal antibody capable of distinguishing human basal cells and malignant squamous cells from other cell types which may be present in the above monoclonal antibody, which second antibody is labeled with a detectable label.

The excised specimen, e.g., the section of skin, is contacted with the first monoclonal antibody under conditions for binding of the antibody to malignant tumor cells. The incubation is generally conducted in an aqueous medium such as, for example, phosphate buffered saline containing a small amount of sodium azide, in a suitable container such as, for example, a glass petri dish, for a period from about 15 to 30 minutes at a temperature of from about 20° to 30° C. The amount of antibody employed is usually sufficient to provide detectable binding, i.e., to provide a detectable number of complexes between the antibody and the antigen site in question.

Following the incubation, the section is washed to reduce or eliminate non-specifically bound antibody and then is examined to observe the above-mentioned complexes which result from binding of the monoclonal antibody to the cells of the specimen possessing the antigenic site. The binding is related to the presence of residual tumor cells in the skin. Accordingly, binding is determined, for example, by contacting the specimen with a labeled specific binding partner for the monoclonal antibody. The label is capable of producing a detectable signal and may be a radioactive label, a chromophore such as a fluorescer, an enzyme, or the like.

An example of a technique employing the above approach is immunofluorescence staining. In this technique frozen sections of skin are fixed on a glass slide with acetone and are incubated with the monoclonal antibody in, for example, a petri dish. After washing with an appropriate buffer such as, for example, phosphate-buffered saline, the skin section is placed on a petri dish and contacted with the labeled specific binding partner for the monoclonal antibody, which may be, for example, a labeled antibody specific for the monoclonal antibody employed. Since, for the most part, the monoclonal antibody will be derived from a murine source, a labeled antimouse immunoglobulin specific for the monoclonal antibody may be employed. Such immunoglobulins may be raised according to standard techniques by injecting a suitable host with murine antibody, waiting for an appropriate time, and harvesting the antimouse immunoglobulins from the blood of the injected host.

After a second washing of the slide with, for example, an aqueous buffer, the sections may be covered with a fluroescent antibody mounting fluid and a coverslip and then examined with a fluorescence microscope to determine the binding of the monoclonal antibody to the skin section. The determination of the binding also may include an identification of the location of such binding within the specimen.

The binding of the monoclonal antibody to the specimen may also be determined by employing a monoclonal antibody which is covalently conjugated to a label capable of producing a detectable signal, such as a radioactive entity, a chromophore including dyes and fluorescers, or an enzyme. The number of labels employed per antibody is generally determined by the requirements of the diagnostic method in which the labeled antibody is employed and the availability of sites for linking the label to the antibody.

Method for conjugating labels to antibodies and antibody fragments are well-known in the art. Such methods may be found in U.S. Pat. Nos. 4,220,450; 4,235,869; 3,935,074; and 3,996,345.

Another example of a technique in which the monoclonal antibody of the invention may be employed is immunoperoxidase labeling (Warnke et al, *J. Histochem. Cytochem,* 28:771-776, 1980). The tissue to be tested is fixed with a suitable solvent, such as acetone, on a support, such as a glass slide. Next, the tissue is incubated with the monoclonal antibody and then washed free of unbound antibody. Then, the tissue is incubated with biotin-conjugated anti-mouse IgG, washed to remove unbound antibody, combined with avidin conjugated horseradish peroxidase, washed to remove unbound conjugate, and then treated with substrate for the enzyme. Following this treatment the slide is examined for a detectable signal.

It has also been found that the VM-2 antibody may be used in a method of determining the presence of a malignant condition in an exfoliative cell specimen obtained from a locus of interest in a mammalian host. This method is disclosed and claimed in patent application No. DO-24290 entitled "Method for Determining the Presence of Malignant Cells" filed on even date herewith. By the term "exfoliative" is meant that the specimen comprises isolated cells or clumps of cells obtained by scraping or washing the surface of tissue, which cells are removed individually or in scales or laminae. The exfoliative cell specimen is to be distinguished from excised tissue such as that obtained by biopsy. The exfoliative cell speciman obtained from the locus is characterized in that a certain antigenic site is usually found in the specimen only when a malignant condition is present. In one embodiment this antigenic site shares determinants with an antigenic site of a normal cell that is not usually expected to be present in the exfoliative cell speciman. The speciman is contacted with an antibody that is specific for the aforementioned antigenic site. The antibody is capable of distinguishing over other cell types which are usually found in the specimen. Contact between the specimen and the antibody is made under conditions for binding of the antibody to the antigenic site. After contact, the presence or absence of binding of the antibody to the antigenic site is determined and is related to the presence of a malignant condition at the locus.

An exfoliative cell specimen is obtained from a locus of interest, i.e., a locus on or in a mammalian host, which locus may or may not have a malignant condition. The specimen may be obtained, for example, by scraping or washing of tissue at the locus. The locus may have membranes covered with squamous cells or with non-squamous cells. Depending on the nature of the tissue involved, or the location of the tissue as the case may be, one may collect an exfoliative body fluid, such as, for example, sputum, which body fluid has been in contact with, and may be said to have washed, the tissue at the locus. The exfoliative cell specimen may be obtained in accordance with the usual techniques of exfoliative cytology. In the detection of cervical carcinoma, for example, a scraping from the cervix would be taken. To determine the presence of malignancy in the lung, a sputum sample would provide the exfoliative cell specimen to be used in the present method. The method finds utility in the detection of a malignant condition in exfoliative cell specimens from the cervix, vagina, uterus, bronchus, prostate, gastro-intestinal tract including oral pharynx, mouth, etc., and exfoliative cell specimens taken from impressions of the surface of tumors or cysts, the cut surface of biopsy specimens, especially lymph nodes, and serous fluids.

The exfoliative cell specimen is next contacted with the aforementioned VM-2 antibody under conditions for binding of the antibody to the specific antigenic site in the specimen to form antigen-antibody complexes. Ths antigenic site may be present on cells or cell fragments in the specimen. Generally, the specimen is placed on an appropriate support, such as, for example, a slide, usually glass, or some other suitable material. The exfoliative cell specimen is generally smeared on the slide to provide a thin layer of the specimen on the surface of the slide. The contact between the antibody and the specimen is generally carried out in an aqueous buffered medium. The buffers which may be employed include phosphate, tris, bicarbnate, etc. The pH is related to the nature of the specimen and the antibody, and is generally in the range of from about 5 to 9. The aqueous medium may additionally contain organic polar solvents in an amount of from about 0 to 40%. The organic polar solvents are water soluble and generally have from about 1 to 10 carbon atoms and from about 1 to 4 oxygen atoms. The antibody will be present in the aqueous medium at a concentration of about 1 to 100 μg/ml, preferably from about 10 to 20 μg/ml. The temperature during the contact of the specimen with the antibody is usually from about 4° to 40° C., preferably about 10° to 30° C. The period of contact is usually from about 15 to 120 minutes, preferably from about 30 to 60 minutes.

After the period of contact between the specimen and the antibody, the support is generally treated to remove unreacted antibody. Normally, this is accomplished by washing the support with an aqueous, usually buffered, medium. In general, the amount of wash solution should be sufficient to remove the unreacted antibody.

Next, the presence of binding of the antibody to the antigenic site in the specimen, which binding is related to the presence of a malignant condition at the locus, is observed. That is, the specimen is examined to determine the number Of antigen-antibody (immune) complexes formed. It should be noted that in some instances very small numbers of the antigenic site in question may be found in the exfoliative cell specimen. However, in a malignant condition, large numbers of the antigenic site will be present and this latter condition is readily distinguishable by this method over a non-malignant condition because a large number of antigen-antibody complexes will be measurable where a malignant condition exists. To made the determination of the presence of binding, means for producing a detectable signal is incoporated into the assay system. For example one may conjugate the antibody employed in the assay to a label which is capable of producing a detectable signal. The label may be a radioactive entity, a chromophore including dyes and fluorescers, an enzyme, or the like. The number of labels employed for the antibody is generally determined by the requirements of the method of the present invention and the availability of sites for linking the label to the antibody.

Alternatively, one may contact the washed slide with a labeled specific binding partner for the antibody, which may be, for example, a labeled antibody specific for the antibody employed. Where the monoclonal antibody is derived from a murine source, a labeled anti-mouse immunoglobulin specific for the antibody employed in the method may be used. Such immunoglobulins may be raised according to standard techniques by injecting a suitable host with the monoclonal antibody, waiting for an appropriate time, and harvesting the anti-mouse immunoglobulins from the blood of the injected host. When a labeled specific binding partner for the antibody is employed, the slide must be washed again with an aqueous medium prior to examining the slide for fluorescence.

To determine the presence of binding between the antibody and the cell specimen where a fluorescer label is used, one may examine the slide for fluorescence, usually employing a fluorescence microscope. Where a label other than a fluorescer is employed, one may examine the slide or the specimen for the formation of a precipitate, a color, or the like.

The above description is directed primarily to the use of the antibodies of the invention in immunofluorescence techniques. However, the antibodies of the invention may be used in most assays involving antigen-antibody reactions. The assays may be homogeneous or heterogeneous. In a homogeneous assay approach, the specimen is lysed and clarified to remove debris. The immunological reaction usually involves the specific antibody, a labeled analyte, and the sample of interest. The signal arising from the label is modified, directly or indirectly, upon the binding of the antibody to the labeled analyte. Both the immunological reaction and detection of the extend thereof are carried out in a homogeneous solution. Immunochemical labels which may be employed include free radicals, fluorescent dyes, enzymes, bacteriophages, coenzymes, and so forth.

In a heterogeneous assay approach, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal includes the use of radioactive labels, fluorescers, enzymes, and so forth. Exemplary of heterogeneous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

The invention also includes a diagnostic kit for carrying out the method disclosed above. In one embodiment, the diagnostic kit comprises (a) a monoclonal antibody more specifically defined above and (b) a conjugate of a specific binding partner for the above monoclonal antibody and a label capable of producing a detectable signal. The reagents may also include ancillary agents such as buffering agents and protein stabilizing agents, e.g., polysaccharides and the like. The diagnostic kit may further include, where necessary, other members of the signal producing system of which system the label is a member, agents for reducing background interference in a test, control reagents, apparatus for conducting a test, and the like. In another embodiment, the diagnostic kit comprises a conjugate of a monoclonal antibody of the invention and a label capable of producing a detectable signal. Ancillary agents as mentioned above may also be present.

The antibodies of the invention may be used therapeutically where binding to normal basal cells would not be a problem. For therapeutic use the antibodies are bound to a toxin to form an immunotoxin or to a radioactive material to form a radiopharmaceutical. Methods for producing immunotoxins and radiopharmaceuticals of antibodies are well-known.

EXAMPLES

The invention is further demonstrated by the following illustrative Examples. A number of procedures employed will be described first.

Cellular Enzyme Linked Immunosorbent Assay (ELISA)

(a) Cell lines: Human foreskin fibroblasts (HFF) were established from primary cultures derived from circumcisions; cells were used between transfers 4 to 10. Peripheral blood lymphocytes, mononuclear cells and erythrocytes were obtained from healthy volunteers. The A-431 vulvar carcinoma cell line and A-549 bronchial carcimona cell line and murine BALB/c 3T3 fibroblasts were obtained from Oncogen, Seattle, Wash. Hela cervical carcinoma cells, GH3 rat pituitary tumor cells, normal rat kidney fibroblasts (NKR), Daudi human B lymphoma, Molt T lymphoma and P 388 D1 murine macrophage cell line were obtained from the ATCC. Skin squamous cell carcinoma (SCC) cell line were obtained from Dr. N. Fusenig, Heidelberg, German, and bovine and rabbit aortic endothelial cells (EC) were prepared according to standard techniques. Bovine venous EC were obtained from the University of California at San Francisco, and murine capillary EC from Dr. A. Curtis of Glasgow, Scotland. All tissue culture cells were grown in Dulbecco's minimal essential medium (DMEM, MA Bioproducts) containing 10% fetal calf serum (Hyclone).

(b) Adherent cells were grown to subconfluence in 96 well Linbro dishes: cells growing in suspension were allowed to adhere to the 96 well dishes for 30 min at 37° C. after precoating of the wells with 50 µl/well of a 0.1% poly L-lysine (Miles Laboratores, Inc.) solution in phosphate buffered saline (PBS). Cells were then fixed in the wells for 5 min at room temperature with 0.25% glutaraldehyde (Sigma Chemical Corporation) and washed 3 times with PBS. Dishes where either used immediately or stored at 4° C. in humidified chambers. Cells were incubated at 37° C. for 2 h with monoclonal antibody, washed with PBS containing 0.1% bovine serum albumin (PBS-BSA) and further incubated with rabbit anti-mouse (Ig) immunoglobin antibodies coupled to peroxidase (Zymed or Cappel) at 37° C. for 2 h. After washing with PBS-BSA cells were incubated for 10 min at room temperature with 1 µg/ml orthopenylenediamine and 0.03% $H_2O_2$ in 0.1M citrate buffer, pH 4.5. Optical density (O.D.) at 630 nm of individual wells was determined on a Dynatec ELISA plate reader. O.D. readings tenfold higher than that of controls (no first and/or no second antibody incubation) was considered to reflect significant binding of the antibody to the cells.

Immunofluorescence (IF) Staining of Frozen Section of Skin or Dispersed Cells The binding of antibodies to epidermal cells in situ was determined by IF using rabbit anti-mouse fluorescein isothiocyanate conjugated Ig (R/M-FITC). This reagent had been adsorbed on dispered human skin cells. Frozen sections of skin were incubated with monoclonal antibody (either VM-1 or VM-2) in humidified glass petri dishes for 15 minutes at room temperature, washed with PBS, labeled with R/M-FITC for 15 minutes and washed with PBS (Harrist and Mihm, *Hum. Pathol.*, 10:625–653, 1979). Sections were covered with fluorescent antibody mounting fluid (DIFCO) and a glass coverslip and examined with a Zeiss fluorescence microscope. Trypsinized cell suspensions were labeled in a similar manner. Aliquots of labeled cells were resuspended in PBS, placed on a slide, covered with a glass cover slip and examined with a fluorescence microscope.

Immunoperoxidase (IP) Labeling of Frozen Skin Sections

Frozen sections of human skin were labeled using the immunoperoxidase staining technique (Warnke et al., *J. Histochem. Cytochem.*, 28:771–776, 1980). Briefly, the tissue was fixed with acetone, incubated with monoclonal antibody (either VM-1 or VM-2), washed with PBS, incubated with biotin-conjugated goat anti-mouse IgG (G/M-IgG)(Tago, Inc.), washed with PBS, labeled with avidin conjugated horseradish peroxidase, washed with PBS and $H_2O$, incubated with fresh diaminobenzidine solution and rinsed with PBS and $H_2O$. All incubations were at room temperature. The sections were processed in 0.5% $CuSO_4$ solution, counterstained with Giemsa, cleared and mounted. Slides were examined with a light microscope.

$^{35}S$-Methionine Labeling of VM-2 Antibody

Hybridoma cells producing VM-2 antibody were seeded into a microtiter well in methionine free DMEM containing 25 mM Hepes buffer, 4 mM L-glutamine, 4.5 gm/l glucose, 10 mM non-essential amino acids, 100 units/ml penicillin, 100 µg/ml streptomycin and 15% heat inactivated newborn calf serum (NCS). The cells were contacted for 6 hrs with 0.1 mCi $^{35}S$ methionine at 37° C., the supernatant removed and centrifuged to remove cells.

Isotype Determination of VM-2

(a) Ouchterlony immunodiffusion

An aliquot of supernatant of VM-2 hydridoma cells was placed into the center well of a 2% agar plate. Monospecific rabbit anti-mouse Ig isotypes antibodies (Meloy) were placed in the outer wells and the plate was incubated for 2 h at room temperature and overnight at 4° C.

(b) Flexible polyvinylchloride 96 well plates (Costar) were coated with 0.1 mg/ml goat anti-mouse Ig antibodies for 2 h at 37° C. and countercoated with a 3% BSA solution for 2 h at 37° C. VM-2 hydrodoma supernatant was then incubated at 37° C. for 2 h. After washing with PBS-BSA plates were incubated at 37° C. for 2 h with monospecific rabbit anti-mouse Ig isotype antibodies coupled to peroxidase (Zymed). After washing, plates were incubated with 1 mg/ml orthophenylenediamine and 0.03% $H_2O_2$ in 0.1M citrate buffer pH 4.5. Optical density at 630 nm was determined on a Dynatec Elisa plate reader.

Staphylococcal Protein A Binding Assay

Microtiter walls were incubated with 5% NCS in PBS plug 0.02% $NaN_3$ and the supernatant was aspirated. Twenty-five µl of a suspension of epidermal cells ($2 \times 10^7$ cells/ml) were added to each well and incubated with 25 µl of VM-2 for 1 hr at room temperature. The plates were centrifuged at 1200 rpm for 7 min, washed twice with 50% $NCS/PBS/NaN_3$ and 25 µl $^{125}I$-staphylococcal proteing A (about 50,000 cpm/25 l) were added. The plates were incubated for 1 hr at 25° C., washed twice with 5% $NCS/PBS/NaN_3$ and dried. The bottom of the wells were cut off and counted in a gamma counter.

Immunoprecipitation Studies

SCC, A-431, Hela and HFF cells were grown to subconfluence in 100 mm tissue culture dishes in DMEM containing 10% FCS. Cells were incubated at 37° C. for 4 h with 100 µCi [$^{35}S$]-methionine in DMEM deficient in methionine (GIBCO) containing 10% dialyzed FCS. Cells were washed with PBS-BSA and lysed with PBS containing 0.5% Triton X-100 (Sigma) for 30 min at 4° C. Lysates were centrifuged for 4 min at 10,000xg in an Eppendorf centrifuge to remove cell nuclei and debris. Lysates were then incubated at 4° C. for 2 h with 10 µg VM-2 antibody and antigen-antibody complexes were precipitated with 100 µg goat antimouse Ig antibody by overnight incubation at 4° C. and centrifugation. Immunoprecipitates were washed 4 times with PBS-SBA containing 0.1% Triton X-100 and solubilized in 10 ml Laemli sample buffer by boiling for 2 min. Antigen analysis was performed on 5–15% acrylamide gradient one dimensional sodium dodecyl suplate polyacrylamide slab gels. Gels were run at 30 mA constant intensity for 6 h, stained with Coomassie Brilliant Blue, destained, treated with Enhance ® (NEN), dried and processed for fluorography for one or two days. Borohydride tritiated protein mixtures were prepared using standard techniques and were run in parallel to allow apparent molecular weight determinations.

EXAMPLE 1

Preparation of VM-2 Antibody

A. Isolation and Culture of Human Epidermal Cells

Single cell suspensions of skin cells were prepared from split thickness skin from psoriatic plaques removed with a keratotome (Davol) preset at 0.015 inches or from skin obtained at surgery (for keratinocyte cultures). Full thickness skin obtained at surgery was trimmed, cut into 1×5 mm strips and split-cut with a Castroviejo keratotome set at 0.1 mm. Strips of split-thickness skin were treated for 25 min at 37° C. with 0.3% trypsin (ICN Pharmaceuticals) in 0.8% NaCl, 0.04% KCl, 0.1% glucose, pH 7.3, plus 0.1% EDTA. The skin slices were washed, transferred to complete growth medium consisting of Dulbecco's Minimum Essential Medium (DMEM) plus 10% heat inactivated fetal calf serum (FCS), 50 $\mu$G/ml gentamicin, 2 mM L-glutamine, 50 units/ml penicillin, 50 $\mu$g/ml streptomycin and the basal and malpighian cells were released into the medium by gentle agitation. For culture, $2\times10^6$ viable, round refractile cells from normal skin were plated on a collagen thin gel coated 3.5 cm petri dish (Flow Labs) and incubated in 5% $CO_2$:95% air at 37° C. Viability was determined by trypan blue exclusion.

B. Production of Antibody

Using standard techniques (Köhler and Milstein, supra), MOPC-21 myeloma cells were fused with spleen cells obtained from a BALB/c(NIH strain) mouse. To immunize and boost the mouse, keratotome sections from psoriatic plaques from 2 unrelated donors were incubated in trypsin/EDTA as described above. The dispersed cells were washed once with complete growth medium, resuspended in PBS and injected into the mouse intraperitoneally. The antibodies produced by fused cells were screened by the immunofluorescence technique described above using frozen sections prepared from both normal skin and skin obtained from psoriatic plaques. Skin for frozen sections from psoriatic plaques was obtained using a local anesthetic and a 3 mm biopsy punch.

EXAMPLE 2

A. Characterization of VM-2 Antibody

VM-2 was cloned and then subcloned 2 times. The last two cultures were derived from microtiter wells for which serial dilutions predicted ½ cells/well. Cells were grown in large scale in 75 cm² tissue culture flasks for 12 h in the absence of fetal calf serum. Conditioned medium was precipitated with 35% saturated ammonium sulfate for 4 h at 4° C. Precipitates were extensively dialyzed against PBS and yielded 10–20 $\mu$g/ml medium semi-purified VM-2 antibody. Alternatively, $10^7$ VM-2 cells were injected intraperitoneally in pristane treated BALB/c mice. After 10 days ascites fluid was collected, cleared by centrifugation and precipitated with 35% saturated ammonium sulfate. After dialysis VM-2 antibody was further purified by gel chromatography on an LKB ULtragel AcA-34 column. Ascites fluid yielded between 2–5 mg antibody/ml. On one dimensional gel electrophoresis, the antibody consists of two heavy chains of molecular weight of about 50,000 daltons, and two light chains of molecular weight about 25,000 daltons. The antibody does not bind to staphylococcal protein A. On Ouchterlony immunodiffusion, a precipitin band was seen only in the area of the antibody against $\gamma_1$ and anti-7s antibody. Thus, VM-2 is an IgG of the $\gamma_1$ subtype. The $IgG_1$ nature of VM-2 was also confirmed by the solid phase double antibody ELISA procedure described above.

VM-2 does not inhibit cellular growth. Cultures treated with a 1:10 dilution of VM-2 showed about a 4-fold increase in DNA content during the period of culture as did the controls. By contrast in parallel epidermal cell cultures incubated with VM-1 the total DNA content/plate stayed constant or decreased slightly during 13 days in culture.

VM-2 antibodies did not affect the growth of keratinocytes over a six-day period whereas VM-1 antibodies did. VM-2 did not inhibit growth of fibroblasts over a five-day period.

B. The specificity of VM-2 antibody was further assessed by cellular ELISA on various cell types as described above. Results are summarized in Table I.

VM-2 binds to a determinant on an antigenic site present on SCC, A-431, A-549 and Hela cells. Normal fibroblasts, endothelial cells or cells from the hematopoietic lineage are not recognized by the VM-2 antibody.

C.

Upon immunoprecipitation of the VM-2 antibody incubated with lysates of biosynthetically labeled target cells, 2 protein bands, each of apparent molecular weight of approximately 120,000, were revealed by fluorography. Protein bands of similar molecular weight were obtained from SCC, A-431 and Hela cells, although in different relative amounts. No protein was precipitated from control HFF cells under the same conditions.

TABLE I

| Binding of VM-2 Antibody to Cells as Determined by Cellular ELISA | |
|---|---|
| Cell Type | Reactivity with VM-2 Antibody |
| Skin squamous cell carcinoma (human) | +++ |
| A-431, vulvar carcinoma (human) | ++ |
| A-549, bronchial carcinoma (human) | + |
| Hela, cervical carcinoma (human) | +++ |
| Foreskin fibroblasts (human) | − |
| 3T3 fibroblasts (murine) | − |
| Kidney fibroblasts (rat) | − |
| Peripheral blood lymphocytes (human) | − |
| Peripheral blood monocytes (human) | − |
| Erythrocytes (human) | − |
| Molt, T lymphoma (human) | − |
| Daudi, B lymphoma (human) | − |
| P388 $D_1$, macrophages (murine) | − |
| Aortic endothelial cells (bovine, rabbit) | − |

TABLE I-continued

Binding of VM-2 Antibody to Cells
as Determined by Cellular ELISA

| Cell Type | Reactivity with VM-2 Antibody |
| --- | --- |
| Venous endothelial cells (bovine, murine) | — |

At 10 μg/ml VM-2 antibody
+: O.D. > 10 times background
++: O.D. > 20 times background
+++: O.D. > 40 times background

EXAMPLE 3

Detection of Residual Tumor Cells in Microscopically Controlled Surgery (MCS)

A.

Frozen sections of skin were prepared from tissue obtained at surgery, which was snap-frozen on a chuck placed on dry ice using OCT compound (Lab-Tek Division, Miles Laboratories Inc., Naperville, Ill.). Sections were cut with a microtome. The binding of antibodies to epidermal cells in situ was determined by immunofluorescence staining using rabbit antimouse fluorescein isothiocyanate-conjugated Ig (R/M-FITC). This reagent was absorbed on dispersed human skin cells. Frozen sections of skin were incubated with monoclonal antibody (either VM-1 or VM-2 antibody) in humidified glass petri dishes for 15 min at room temperature, washed with phosphate-buffered saline (PBS), labeled with R/M-FITC for 15 min, and washed with PBS. Sections were covered with fluoroescent antibody mounting fluid (Difco laboratories Inc., Detroit, Mich.) and examined with a Zeiss fluorescence microscope.

B.

Prozen sections of human skin were labeled, using the IP staining technique. Briefly, the tissue was fixed with acetone, incubated with VM-1 or VM-2 antibody, washed with PBS, incubated with biotin-conjugated goat antimouse IgG (G/M-IgG) (Tago, Inc., Burlingame, Calif.), washed with PBS, labeled with avidin-conjugated horseradish peroxidase, washed with PBS and H₂O, incubated with diaminobenzidine (DAB) solution, and rinsed with PBS and H₂O. All incubations were at room temperature. The sections were processed in 0.5% CuSO₄ solution, counterstained with Giemsa, cleared, and mounted.

C. Results and Discussion

In tissue from seven of seven different patients with basal cell carcinoma (BCC), including a morphea form tumor, and two patients with squamous cell carcinoma (SCC), VM-1 and VM-2 antibody, respectively, allowed distinct staining of the tumor cells. Staining was uniform in all of the BCC and in one of the SCC specimens. In the other SCC, antibody binding was most dense at the periphery of large tumor islands, and less dense in the centers, where the cells appeared more squamoid. In smaller tumor nests the staining was quite uniform. Small islands of tumor were easily detectable in all specimens by both IP and IF technics. Control staining with a murine myeloma antibody of the same isotype as VM-1 and VM-2 did not delineate the tumor cells.

EXAMPLE 4

Determination of the Presence of Malignant Cells in Exfoliative Cell Specimens Obtained from the Cervix Cervical smears were obtained from 20 healthy volunteers on routine gynecological examination and from 20 patients with invasive squamous cervix carcinoma established independently by conventional cytology of biopsies. The smears were acetone dipped for 5 min at room temperature, air "dried" and kept desicated at −70° C. until use. The smears were then covered with 200 μl of 10–50 μg/ml fluoresceinated VM-2 antibody, prepared as described in Example 3, for 30 min at room temperature in a humidified chamber. The smears were extensively washed in PBS by transfer in several Coplin jars, mounted in 50% glycerol in PBS and observed with a Zeiss Universal fluroescence microcope. No cellular staining was observed for any of the smear obtained from the healthy volunteers. In smears of 20 out of 20 patients with invasive squamous cervix carcinoma an intense membrane fluorescence staining was observed on small round cells in the sample. Large squamous cervical cells with pycnotic nuclei were not stained, nor were erythrocytes and polymorphs found in most of the samples. For some patients, available duplicate smears were stained according to the conventional Papanicolaou technique. The small round cells stained by the VM-2 antibody were confirmed in these samples as possessing neoplastic features (altered nucleus/cytoplasmic ratio and basophilic, abnormal nuclei).

The cell line, designated VM-2, was deposited on Mar. 21, 1984 at the A.T.C.C. (American Type Culture Collection, 12301 Park Lawn Drive, Rockhill, Md. 20852 U.S.A.) and received accession number HB 8530.

The invention has been described in detail with particular reference to the above embodiments. It will be understood, however, that variations and modifications can be affected within the spirit and scope of the invention.

What is claimed is:

1. A monoclonal antibody that binds to an antigenic site on a protein characteristic of a human basal cell surface and a human malignant squamous cell and binding fragments of said antibody, wherein said protein is characterized as having a molecular weight of about 120,000 daltons as determined by polyacrylamide gel electrophoresis.

2. The monoclonal antibody of claim 1 obtained from a hybrid continuous cell line having the identifying characteristics of A.T.C.C. HB8530.

3. A hybrid continuous cell line having the identifying characteristic of A.T.C.C. HB8530.

4. A method for determining the presence of a malignant condition in tissue, which comprises
   (a) contacting a specimen of tissue suspected of a malignant condition with an antibody that binds to an antigenic site characteristic of a human basal cell, said tissue usually not containing normal basal cells, said antibody being capable of binding to human normal and malignant basal cells and human malignant squamous cells and capable of distinguising such cells from other cell types in said specimen, under conditions for binding of said antibody to said specimen, and (b) observing the presence of binding of said antibody to said specimen, said binding being related to the presence of a malignant condition in said tissue.

5. The method of claim 4 wherein the antibody is an antibody obtained from a hybrid continuous cell line having the identifying characteristics of A.T.C.C. HB8530 or a binding fragment of said antibody.

6. The method of claim 4 wherein the extent of binding is determined by contacting said specimen with a conjugate of a label and specific binding partner for said monoclonal antibody, said label being capable of producing a detectible signal.

7. The method of claim 4 wherein the monoclonal antibody is conjugated to a label capable of producing a detectible signal.

8. The method of claim 6 wherein the labeled specific binding partner for said monoclonal antibody is an antibody specific for said monoclonal antibody.

9. The method of claim 7 wherein the label is a chromophore.

10. In an in vitro method of microscopically controlled surgery to remove a tumor wherein a clinically visible tumor is removed surgically and the next layer of tissue is excised and checked for residual tumor cells with a light microscope, the improvement wich comprises using a monoclonal antibody that binds to an antigenic site characteristic of a human normal and malignant basal cell surface and a human malignant squamous cell to detect residual tumor cells, the area adjacent said tumor cells usually not containing normal basal cells.

* * * * *